(12) United States Patent
Kumoyama et al.

(10) Patent No.: US 8,388,635 B2
(45) Date of Patent: Mar. 5, 2013

(54) CATHETER HAVING AN ARRANGEMENT FOR REMOVING AN OCCLUDING OBJECT

(75) Inventors: Kenichi Kumoyama, Ashigarakami-gun (JP); Junko Kuniyasu, Ashigarakami-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/335,068

(22) Filed: Dec. 22, 2011

(65) Prior Publication Data

US 2012/0116430 A1    May 10, 2012

Related U.S. Application Data

(63) Continuation of application No. PCT/JP2010/066206, filed on Sep. 17, 2010.

(30) Foreign Application Priority Data

Sep. 29, 2009  (JP) ................................. 2009-225299

(51) Int. Cl.
*A61B 17/22* (2006.01)
(52) U.S. Cl. .................... 606/159; 606/170; 606/180
(58) Field of Classification Search .................. 606/159, 606/127, 128, 180, 79–85, 167, 170, 171, 606/179, 166, 107, 108; 604/22, 35; 175/92, 175/106, 319, 331, 334, 336, 341, 348
See application file for complete search history.

(56) References Cited

U.S. PATENT DOCUMENTS

| | | | | |
|---|---|---|---|---|
| 2,834,578 | A | * | 5/1958 | Carr ............................... 175/237 |
| 4,811,735 | A | * | 3/1989 | Nash et al. .................... 606/128 |
| 4,950,277 | A | * | 8/1990 | Farr ............................... 606/159 |
| 6,190,383 | B1 | * | 2/2001 | Schmaltz et al. ................ 606/41 |
| 6,253,862 | B1 | * | 7/2001 | Overstreet et al. ............ 175/374 |
| 6,482,209 | B1 | | 11/2002 | Engh |
| 6,537,279 | B1 | | 3/2003 | Michelson |
| 2001/0004026 | A1 | * | 6/2001 | Lockstedt et al. ............ 175/431 |
| 2002/0058956 | A1 | | 5/2002 | Honeycutt |
| 2002/0169467 | A1 | * | 11/2002 | Heitzmann et al. ........... 606/159 |
| 2003/0078586 | A1 | * | 4/2003 | Shapira ........................... 606/80 |
| 2007/0265648 | A1 | * | 11/2007 | Cohen .......................... 606/159 |
| 2008/0004643 | A1 | * | 1/2008 | To et al. ........................ 606/159 |
| 2008/0140080 | A1 | * | 6/2008 | Strehl ............................. 606/83 |
| 2009/0023988 | A1 | * | 1/2009 | Korner et al. ................. 600/106 |
| 2009/0031871 | A1 | | 2/2009 | Malandain |
| 2009/0182362 | A1 | | 7/2009 | Thompson et al. |
| 2010/0089576 | A1 | * | 4/2010 | Wideman et al. .......... 166/272.6 |

FOREIGN PATENT DOCUMENTS

WO    2009/036818 A1    3/2009

OTHER PUBLICATIONS

Extended European Search Report dated Nov. 19, 2012 for 10820393.6.

* cited by examiner

*Primary Examiner* — Ryan Severson
*Assistant Examiner* — David Eastwood
(74) *Attorney, Agent, or Firm* — Dorsey & Whitney LLP

(57) ABSTRACT

Exemplary embodiments of the present disclosure can provide a catheter which can include a removal mechanism which can excavate a tubular-organ occluding object. For example, the exemplary catheter can include: a sheath portion which can have a elongated lumen insertable into a tubular-organ. The catheter can further include an insertion member which can have a second elongated lumen which can be arranged free, slidably, and rotatably with respect to the lumen of the sheath portion. The catheter can also include a removal mechanism configured to remove a occluding object of the tubular-organ. The removal mechanism can include a support portion arranged at a distal portion of the insertion member and a plurality of rotating arrangements having at least one blade edge configured to excavate the occluding object. The support portion can have an axis of rotation that intersects an axis of extension of the insertion member.

11 Claims, 10 Drawing Sheets

CATHETER HAVING AN ARRANGEMENT FOR REMOVING AN OCCLUDING OBJECT

CROSS REFERENCE TO PRIOR APPLICATIONS

This application is a continuation application of International Application No. PCT/JP2010/066206, filed on Sep. 17, 2010, which claims priority to Japanese Patent Application No. 2009-225299, filed on Sep. 29, 2009. Both of these applications are hereby incorporated by reference in their entireties.

FIELD OF THE DISCLOSURE

Exemplary embodiments of the present disclosure relate to a catheter having a removal mechanism for a tubular-organ occluding object.

BACKGROUND INFORMATION

In a case in which a tubular-organ inside a living body, for example, a blood vessel of four limbs can be occluded by a foreign object and the blood flow can be disturbed, it can become a cause for inducing necrosis or intermittent claudication of finger tissues of a hand and a foot, which can be caused by ischemia. Therefore, there have been many proposed catheters provided with removal mechanisms for foreign objects (tubular-organ occluding objects).

For example, Japanese unexamined patent publication H11-347040 describes a catheter provided with a rotation cutter including a cylinder sleeve shaped body and a thread extending along a portion of the side surface of the aforesaid body. Japanese unexamined patent publication No. 2000-245741 describes a catheter provided with a cylindrical cutter including a thread extending along a portion of the side surface thereof and a saw blade which is arranged at an end portion and which is formed so as to extend from the center axis to the external side in the radial direction. Japanese unexamined patent publication No. 2004-514463 describes a catheter provided with a compound cutter assembly including a cutter whose distant diameter is fixed and a cutter assembly whose proximal diameter is adjustable. Japanese unexamined patent publication No. 2006-514577 describes a catheter provided with a blade edge assembly including a plurality of blade edge blades which present an appearance shape of approximately a round shape when seen from the axis line direction and of an elliptical or a circular truncated cone shape when seen from the lateral direction, and which are arranged radiation-symmetrically with respect to the center longitudinal axis and also, have differential blade edge surfaces.

However, the rotation surface of the cutters described in Japanese unexamined patent publication H11-347040, Japanese unexamined patent publication No. 2000-245741, Japanese unexamined patent publication No. 2004-514463, and Japanese unexamined patent publication No. 2006-514577 is approximately perpendicular with respect to the drive shaft and the blade edge of the cutter faces the tubular-organ wall, so that it can be easy for the lumen wall to be damaged. Also, since only a single cutter is provided, it may not be possible for the ground occluding object to be ground finely so as to be discharged easily to the outside of the body.

Exemplary embodiments of the present disclosure can, e.g., solve the problem involved in the existing technology mentioned above and can provide a catheter having a removal mechanism which excavates a tubular-organ occluding object inside a living body safely and also more efficiently, and which can also discharge the removed excavated object easily to the outside of the body.

SUMMARY OF EXEMPLARY EMBODIMENTS OF THE DISCLOSURE

An exemplary embodiment of the present disclosure can provide a catheter including:
a sheath portion which can have a lumen elongated in the inside thereof and which can be inserted into a tubular-organ inside a living body;
an insertion member which can have a lumen elongated in the inside thereof and which can be arranged freely slidably and also rotatably with respect to the lumen of the sheath portion; and
a removal mechanism for removing occluding object of the tubular-organ inside the living body, where
the removal mechanism can include a support portion arranged at a distal portion of the insertion member and a plurality of rotation bodies arranged at the support portion and provided with blade edges for excavating the occluding object, and
the support portion can include rotation axis extending to a direction intersecting with the axis of the insertion member.

According to another exemplary embodiment of the present disclosure, it is possible to provide a catheter including:
an insertion member which can have a lumen elongated in the inside thereof and which can be inserted into a tubular-organ inside a living body;
a hollow drive shaft arranged freely rotatably inside the lumen of the insertion member;
a removal mechanism for removing occluding object of the tubular-organ inside the living body, where
the removal mechanism can include a support portion arranged at a distal portion of the insertion member, a plurality of rotation bodies arranged at the support portion and provided with blade edges for excavating the occluding object and
a transmission arrangement for converting the rotation of the drive shaft to the rotation of the rotation body, and
the support portion can include a rotation axis extending to a direction intersecting with the axis of the insertion member.

According to certain exemplary embodiments of the present disclosure, a rotation body can be arranged at a support portion so as to surround a circumference of an axis of an insertion member and can have a rotation axis extending to the direction intersecting with the axis of the insertion member.

Consequently, when removing an occluding object of a tubular-organ inside a living body, the blade edge formed on the rotation body can excavate the occluding object without being faced to a lumen wall. For this reason, it can be possible to reduce damages of the lumen wall during the excavation. Further, points at which the extended lines of the rotation axes of the rotation bodies intersecting with the axis of aforesaid insertion member can be different respectively, so that the positions at which the blade edges of the rotation bodies excavate the occluding object can become different, and it can become possible to realize an excavation of a broad area. In addition, when arranging the approximately conically-shaped rotation bodies having tapers toward the distal directions of the rotation bodies adjacent to each other, the rotation bodies can rotate in the same direction, so that the blade edges of the neighboring rotation bodies move to directions facing mutually. Accordingly, it can be possible to add a larger shearing force onto the occluding object along with going to the bottom surface direction between the neighboring rotation bodies, and it can be possible to grind the excavated object into smaller narrow slips and to make a situation in which the slips can be discharged easily to the outside of the body.

In other words, it can be possible to provide an exemplary embodiment of a catheter which can excavate an occluding object of a tubular-organ inside a living body safely and also more efficiently and which can include a removal mechanism capable of discharging the removed excavated object outside the body easily.

If an excavated-piece suction arrangement is provided in communication with the lumen of the insertion member, if, in the removal mechanism, there is a center opening portion communicated with the lumen of the insertion member, and if the rotation body is positioned at the circumference of the center opening portion, the excavated pieces of the tubular-organ occluding object inside the living body can be introduced to the center opening portion, so that the collection thereof can become easy.

If the shape of the blade edge of the rotation body is constituted so as to pull-in the excavated pieces of the occluding object toward the center opening portion along with the rotation of the rotation body, it can be possible to pull-in the excavated pieces of the tubular-organ occluding object inside the living body toward the center opening portion efficiently.

If a liquid discharge arrangement for discharging liquid is provided at a distal portion of the sheath portion and if the liquid discharge arrangement includes a flow path constituted by a space which formed between the lumen of the sheath portion and the outer circumference of the insertion member, the liquid discharged at the distal portion of the sheath portion can be accompanied by the excavated pieces of the tubular-organ occluding object inside the living body when being pulled-in to the lumen of the insertion member by way of the center opening portion, so that it can be possible to collect the excavated pieces easily and also reliably. In addition, an independent flow path may not be necessary, so that the liquid discharge arrangement can be simplified.

If a drive shaft arranged freely rotatably is provided inside the lumen of the insertion member and if the removal mechanism includes a transmission arrangement for converting the rotation of the drive shaft to the rotation of the rotation body, it can be possible to rotate the rotation body having a blade edge singularly (e.g., independently) and, for example, it can become unnecessary to cause the rotation of the rotation body in a state in which the rotation body can be compressed onto the tubular-organ occluding object inside the living body.

If the transmission means includes a bevel gear arranged at a distal portion of the drive shaft, it can be possible to simplify the structure thereof.

If an excavated-piece suction arrangement is provided in communication with the lumen of the insertion member and the lumen of the drive shaft, and if the removal mechanism includes a center opening portion communicated with the lumen of the insertion member, the excavated pieces of the tubular-organ occluding object inside the living body can be sucked by way of the lumen of the insertion member and the lumen of the drive shaft, so that it can be possible to collect the object excellently.

Still other objects, features and characteristics of the present disclosure shall become clear by referring to exemplary embodiments which are exemplified in the explanations, the attached claims, and the attached drawings hereinafter.

BRIEF DESCRIPTION OF THE DRAWINGS

Further objects, features, and advantages of the present disclosure will become apparent from the following detailed description taken in conjunction with the accompanying drawings showing illustrative embodiments of the present disclosure, in which.

Figure 1:
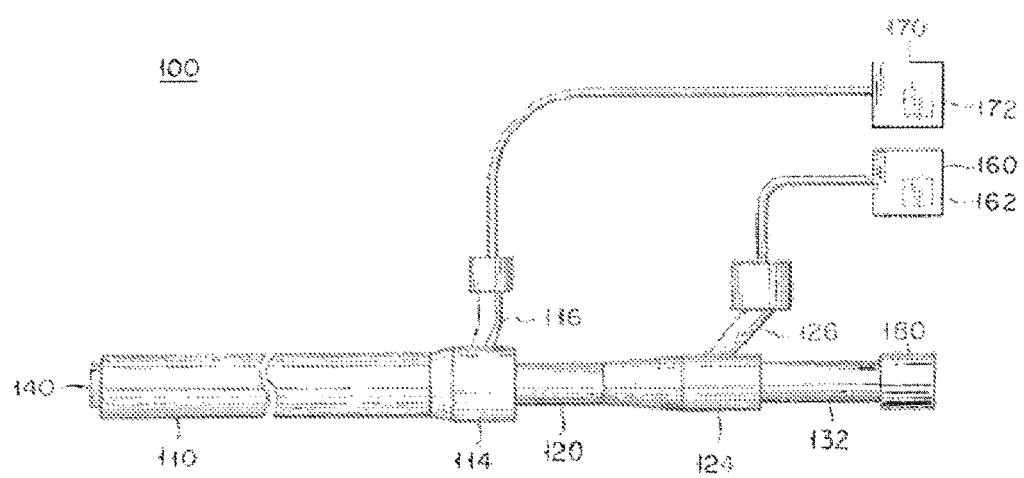
FIG. 1 is a side view of an exemplary catheter according to an exemplary embodiment of the present disclosure.

Throughout the drawings the same reference numerals and characters, if any and unless otherwise stated, are used to denote like features, elements, components, or portions of the illustrated embodiments. Moreover, while the subject disclosure will now be described in detail with reference to the drawings, it is done so in connection with the illustrative embodiments. It is intended that changes and modifications can be made to the described exemplary embodiments without departing from the scope and spirit of the subject disclosure.

DETAILED DESCRIPTION OF EXEMPLARY EMBODIMENTS

Hereinafter, certain exemplary embodiments of the present disclosure will be explained while referring to the drawings.

Figure 2:
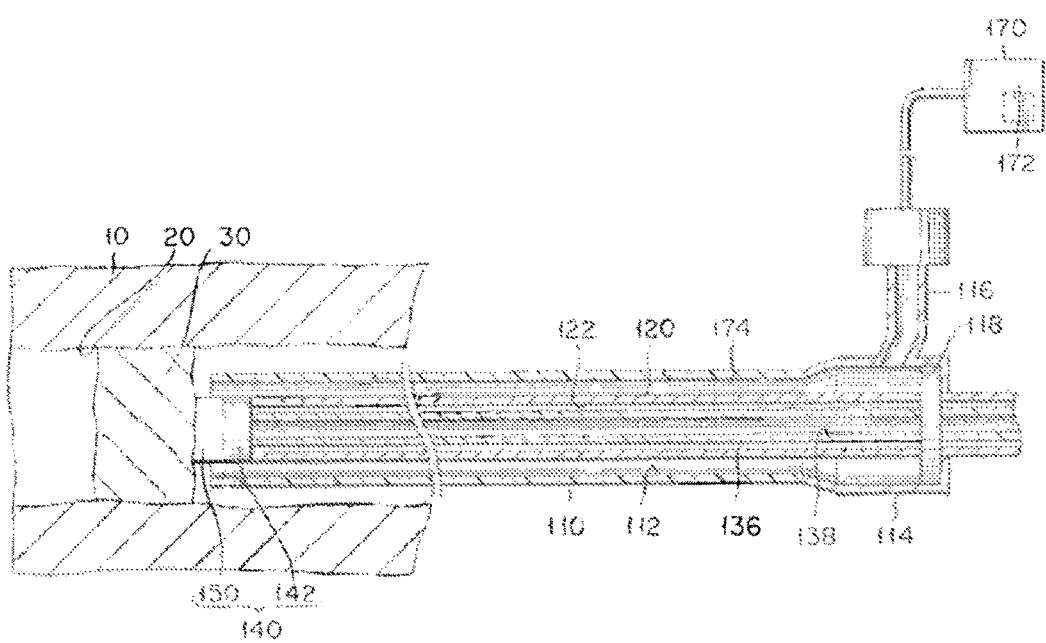
FIG. 2 is a cross-sectional view of an exemplary occluding object removal mechanism and an exemplary liquid discharge system of the exemplary catheter shown in FIG. 1.
Figure 3:
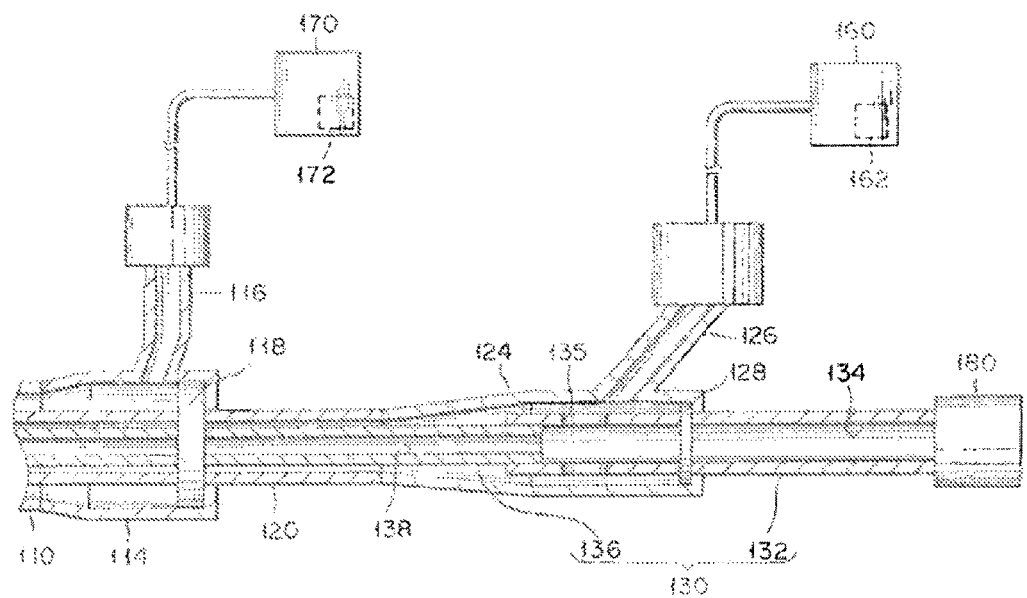
FIG. 3 is a cross-sectional view of an exemplary excavated-piece suction system of the exemplary catheter shown in FIG. 1.

FIG. 1 provides a side view showing an exemplary catheter according to an exemplary embodiment of the present disclosure. FIG. 2 provides a cross-sectional view showing an exemplary occluding object removal mechanism and a liquid discharge system of the exemplary catheter shown in FIG. 1, and FIG. 3 provides a cross-sectional view showing an exemplary excavated-piece suction system of the exemplary catheter shown in FIG. 1.

Exemplary embodiments of the present disclosure can provide an exemplary catheter 100 that can be used for removing an occluding object of a tubular-organ inside a living body and can include a sheath portion 110, an insertion member 120, a drive shaft 130, an occluding object removal mechanism/arrangement 140, an excavated-piece suction system 160, a liquid discharge system 170, and a drive device 180.

The tubular-organ inside the living body can be, for example, a blood vessel in four limbs of a patient who suffers from atheroma arteriosclerosis, and the occluding object can include an atheroma layer which can be formed by neutral fat accumulated in an intima layer of a blood vessel and by lime further deposited thereon and besides that, there can also be cited coagulated aggregate (e.g., thrombus) caused by adhesion or agglomeration of blood platelets, or by coagulation of blood.

The sheath portion 110 can include a hollow tube having a lumen 112 which can be elongated in the inside thereof and can include a distal portion inserted into a tubular-organ 20 inside a living body 10 and a proximal end portion interlinked to a Y-shaped adaptor 114. The Y-shaped adaptor 114 can include a branch port 116 with which the liquid discharge system 170 can be interlinked.

Although there is no limitation in particular, it can be preferable for the outer shape of the sheath portion 110 to be cylindrical and it can be set appropriately in response to the tubular-organ 20 inserted therein.

It can be possible for the material of the sheath portion 110 to include, for example, a high-polymer material such as, e.g.: polyolefin, olefin-based elastomer, polyester, soft polyvinyl chloride, polyurethane, urethane-based elastomer, polyamide, polyamide-based elastomer, polytetrafluoroethylene, fluorine-based elastomer, polyimide, ethylene vinyl acetate copolymer and silicone rubber or the like. The polyolefin can be, for example, polypropylene or polyethylene. The olefin-based elastomer can be, for example, polyethylene elastomer or polypropylene elastomer. The polyamide-based elastomer can be, for example, polyamide elastomer.

In case of forming the sheath portion 110 from a high-polymer material, it can be possible, for example, to improve rigidity thereof through a compounding process by utilizing a pipe of a superelastic alloy, or an embedded coil or an embedded mesh, which can include a metal.

It can be preferable for the distal portion of the sheath portion 110 to have a function as an X-ray contrast marker and, for example, it can be formed by using a resin which contains an X-ray contrast material. The X-ray contrast material can be, for example, a powder such as of tantalum, tungsten carbide, bismuth oxide, barium sulfate, platinum or an alloy thereof, a cobalt alloy and the like.

The insertion member 120 can include a hollow tube having a lumen 122 which can be elongated in the inside thereof and includes a distal portion at which the occluding object removal mechanism 140 can be arranged and a proximal end portion which can be interlinked to a Y-shaped adaptor 124, and can be arranged so as to be freely slidable and also rotatable with respect to the lumen 112 of the sheath portion 110. The proximal end portion of the insertion member 120 can be extended by passing through the Y-shaped adaptor 114 with which the proximal end portion of the sheath portion 110 can be interlinked and, for example, air-tightness can be secured by a sealing device 118 having an O-ring. The Y-shaped adaptor 124 can include a branch port 126 with which the excavated-piece suction system 160 can be interlinked.

For the outer shape of the insertion member 120, there is no limitation as to whether the insertion member is slidable and/or also rotatable inside the lumen 112 of the sheath portion 110, and it can be preferable for the sheath portion to be cylindrical.

It can be possible for the material of the insertion member 120 to include, for example, a metal and a high-polymer material with relatively high rigidity or a material obtained by combining those appropriately and the like. The metal can include, for example, a stainless steel, a Ni—Ti alloy, a Cu—Zn alloy, a cobalt alloy or tantalum. The high-polymer material can include, for example, polyamide, polyimide, ultra high molecular weight polyethylene, polypropylene or a fluorine resin.

The drive shaft 130 can include interlinking a proximal shaft 132 and a distal shaft 136.

The proximal shaft 132 can include a hollow tube having a lumen 134 which can be elongated in the inside thereof and it can be interlinked to a drive device 180 by being extended by passing through the Y-shaped adaptor 124. With respect to the passing-through portion of the Y-shaped adaptor 124 and the proximal shaft 132, air-tightness thereof can be secured, for example, by a sealing device 128 including an O-ring. The proximal shaft 132 can include an opening portion 135 at a region which can be positioned inside the Y-shaped adaptor 124.

The distal shaft 136 can include a hollow tube having a lumen 138 which can be elongated in the inside thereof, can be arranged freely rotatably in the lumen 122 of the insertion member 120, and can be interlinked to a transmission device of the occluding object removal mechanism 140. It can be noted that the distal shaft 136 can be interlinked to the proximal shaft 132 in the vicinity of the Y-shaped adaptor 124. There is no limitation for the outer shape of the distal shaft 136 if the shaft is slidable and/or also rotatable in the inside of the lumen 122 of the insertion member 120.

In consideration of the intensity and rigidity for transmitting the driving force of the drive device 180, it can be possible for the material of the proximal shaft 132 and the distal shaft 136 to include, for example, a metal and a high-polymer material with relatively high rigidity or a material obtained by combining those appropriately and the like.

According to certain exemplary embodiments of the present disclosure, it is possible to provide an exemplary occluding object removal mechanism 140, which can include, for example, a body 142 which can be a support portion arranged at a distal portion of the insertion member 120, a roller hit 150 which can be a excavation portion having first through third cones for removing an occluding object 30 of the tubular-organ 20 inside the living body 10, and a transmission mechanism for converting the rotation of the distal shaft 136 to the rotation of the first to third cones.

The roller bit 150 can accompany the move of the insertion member 120, can be projected from the distal end of the sheath portion 110, and can contact the occluding object 30. The force for excavating the occluding object 30 can be generated by rolling of the roller bit 150 on the occluding object surface depending on the rotation of the insertion member 120 or by transmitting the rotation of the drive shaft 130 (distal shaft 136) to the roller bit 150 through the transmission mechanism. The body 142 can include a center opening portion communicated with the lumen 122 of the insertion member 120.

According to certain exemplary embodiments of the present disclosure, it is possible to provide an exemplary excavated-piece suction system 160, which can be a excavated-piece suction arrangement used for collecting excavated pieces of the occluding object 30 which was removed by the occluding object removal mechanism 140. The excavated-piece suction system 160 can include a suction pump 162 for sucking the excavated pieces of the occluding object 30, can be interlinked to the branch port 126 of the Y-shaped adaptor 124 which can be interlinked to the proximal end portion of the insertion member 120, and can communicate with the lumen 122 of the insertion member 120. The suction pump 162 can be a excavated-piece suction arrangement, which can include a metering pump such as, for example, a diaphragm pump, a squeeze pump (tube pump), a piston pump, a plunger pump and the like.

The region of the proximal shaft 132 which can be positioned inside the Y-shaped adaptor 124 can include the opening portion 135, such that the excavated-piece suction system 160 can communicate with the lumen 134 of the proximal shaft 132 and the distal shaft 136 with which the proximal shaft 132 can be interlinked so that it passes-through the lumen 122 of the insertion member 120, reaches the occluding object removal mechanism 140 and can communicate with the outside.

In other words, it can be possible for the excavated-piece suction system 160 to utilize both sides of the lumen 122 of the insertion member 120 and the lumens 134, 138 of the drive shaft 130 (e.g., proximal shaft 132 and distal shaft 136), and it can be possible to collect the excavated pieces of the occluding object 30 efficiently. If preferred, it can be also possible to form the drive shaft 130 (e.g., proximal shaft 132 and distal shaft 136) to be a solid-core shaft. In this case, it can happen that the excavated-piece suction system 160 utilizes only the lumen 122 of the insertion member 120 for the suction (e.g., collection).

According to further exemplary embodiments of the present disclosure, it is possible to provide an exemplary liquid discharge system 170, which can include a liquid discharge arrangement used for discharging liquid to the distal portion of the sheath portion. The liquid can be, for example, a physiological salt solution. If preferred, it can be also possible to add a thrombolytic agent to the physiological salt solution. The thrombolytic agent can be, for example, urokinase or tissue plasminogen activator (t-PA).

The exemplary liquid discharge system 170 can be interlinked to the branch port 116 of the Y-shaped adaptor 114 to which the proximal end portion of the sheath portion 110 can be interlinked and can be in communication with the lumen 112 of the sheath portion 110. The exemplary liquid discharge system 170 can also include a discharge pump 172 interlinked to a container in which liquid can be maintained and a flow path 174 for discharging the liquid to the distal portion of the sheath portion 110. The discharge pump 172 can be a metering pump such as, for example, a diaphragm pump, a squeeze pump (tube pump), a piston pump, a plunger pump and the like.

The flow path 174 can include a space which can be formed between the lumen 112 of the sheath portion 110 and the outer circumference of the insertion member 120. Thus, the liquid discharged to the distal portion of the sheath portion 110 can be accompanied by the excavated pieces of the occluding object 30 of the tubular-organ 20 inside the living body 10 when being pulled into the lumen 122 of the insertion member 120 by way of the center opening portion of the body 142 of the occluding object removal mechanism 140, so that it can be possible to collect the excavated pieces easily and also reliably. In addition, an independent flow path is not required, so that the liquid discharge system 170 can be simplified.

The drive device 180 can include, for example, a servo motor and it can be configured so that the proximal shaft 132 can be driven freely rotatably. The proximal shaft 132 can be interlinked to the first through third cones by way of the distal shaft 136 and the transmission mechanism. Consequently, it can be possible for the drive device 180 to rotate the first through third cones separately (e.g., independently) and to remove the occluding object 30 of the tubular-organ 20 inside the living body 10. If preferred, it can be also possible for the drive device 180 to be eliminated, and to rotate the drive shaft 130 (e.g., proximal shaft 132) manually.

Figure 4:
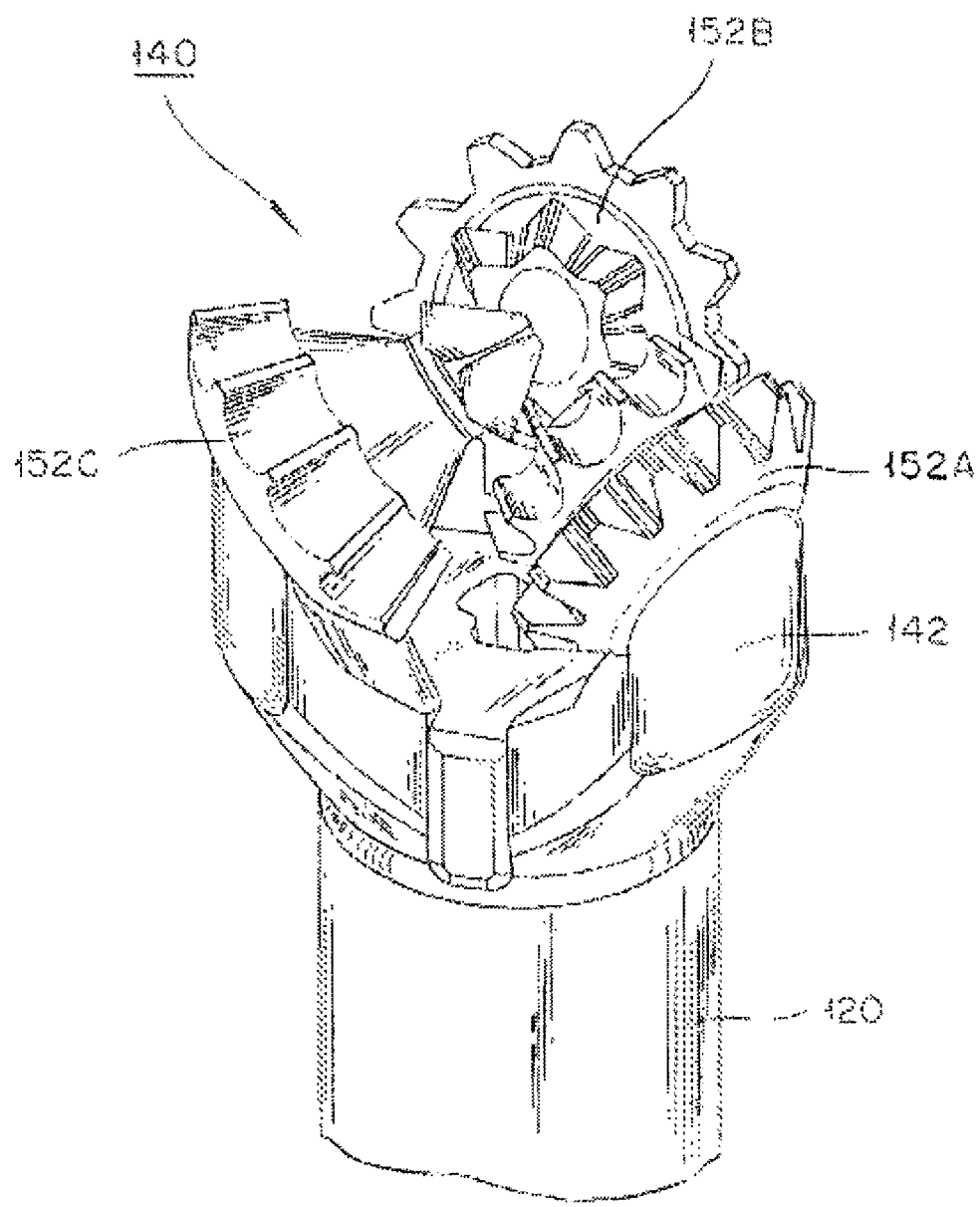
FIG. 4 is an illustration of an exemplary occluding object removal mechanism according to an exemplary embodiment of the present disclosure.
Figure 5:
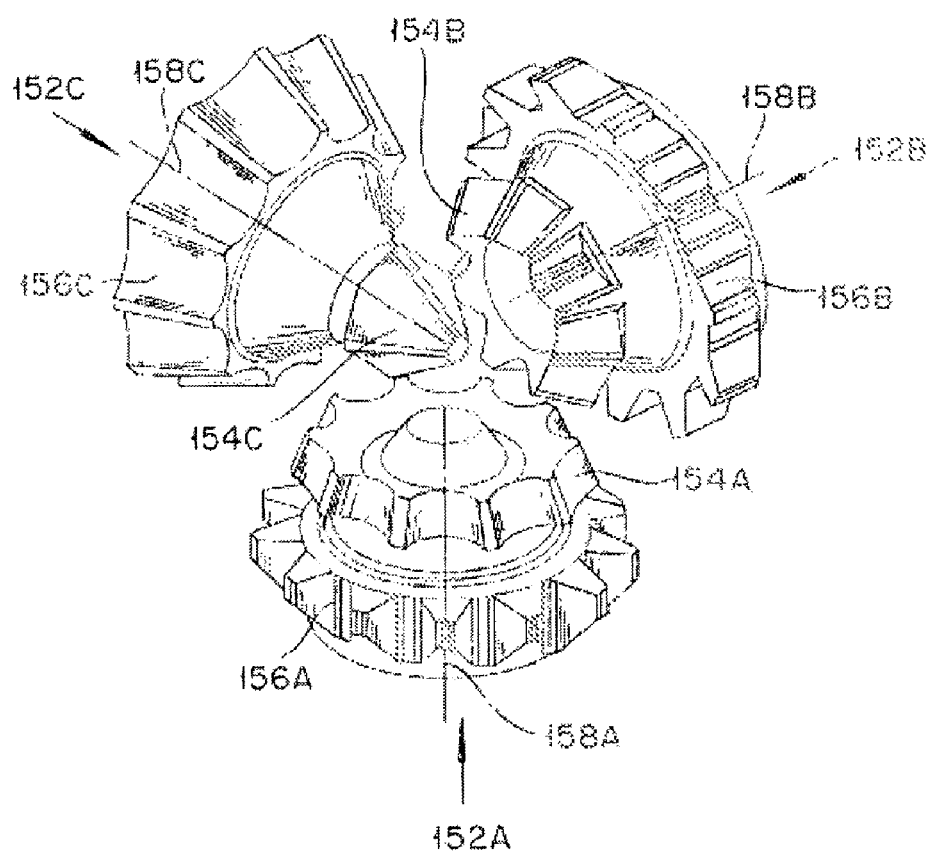
FIG. 5 is a perspective view of the exemplary occluding object removal mechanism shown in FIG. 4.
Figure 6:
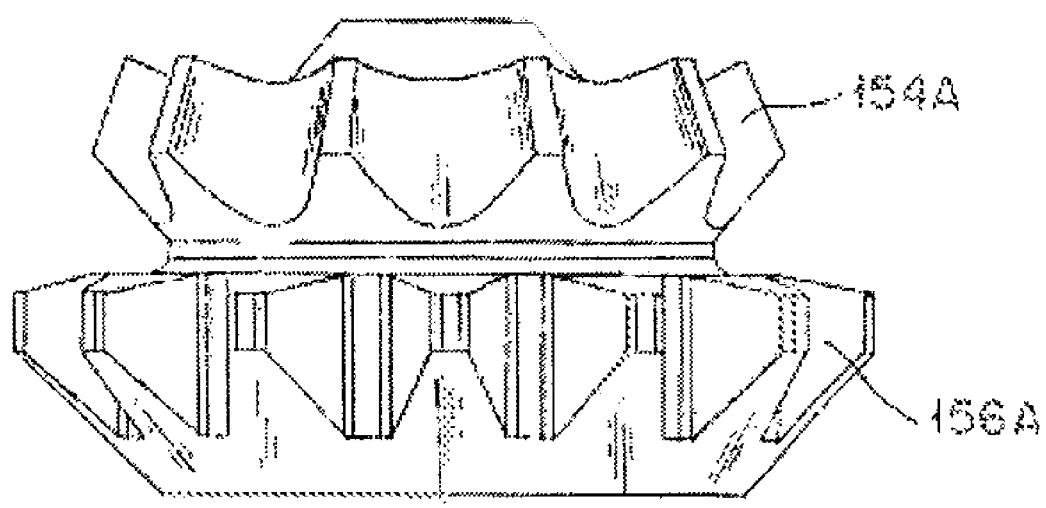
FIG. 6 is a plan view of an exemplary first cone of the exemplary occluding object removal mechanism shown in FIG. 5.
Figure 7:
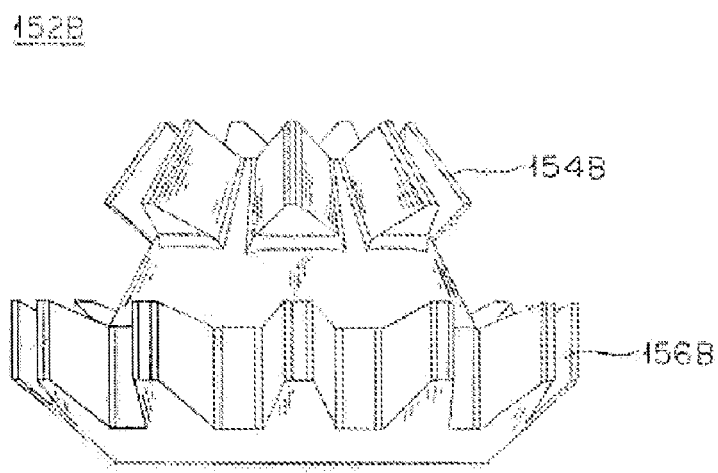
FIG. 7 is a plan view of an exemplary second cone of the exemplary occluding object removal mechanism shown in FIG. 5.
Figure 8:
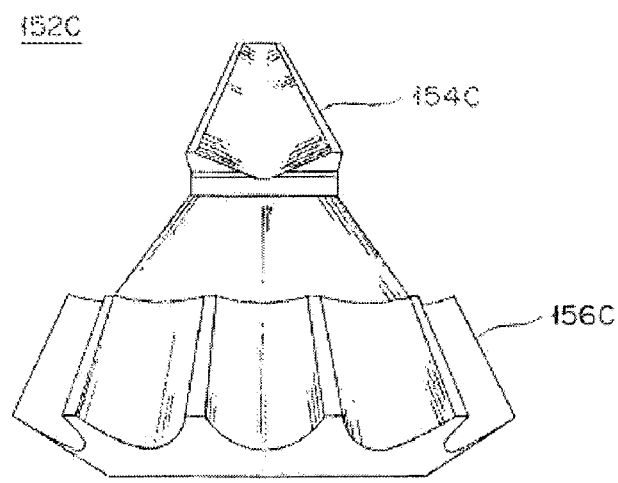
FIG. 8 is a plan view of an exemplary third cone of the exemplary occluding object removal mechanism shown in FIG. 5.

FIG. 4 shows an illustration of an exemplary occluding object removal mechanism according to an exemplary embodiment of the present disclosure, FIG. 5 shows a perspective view of the exemplary occluding object removal mechanism illustrated in FIG. 4, and FIGS. 6 to 8 show plan views of exemplary first through third cones of the exemplary occluding object removal mechanism illustrated in FIG. 5.

The occluding object removal mechanism can include a body 142 disposed at the distal portion of the insertion member 120 and first through third cones 152A-152C, which can be rotation/rotating bodies.

The first through third cones 152A-152C can be arranged, for example, at the body 142 freely rotatably through bearings and can be position-set so as to surround the circumference of an axis A of the insertion member 120, and they include upper-portion blade edges 154A to 154C which can be arranged at the outer circumferences of the top portions thereof, lower-portion blade edges 156A to 156C which can be arranged at the outer circumferences of the proximal portions thereof and rotation axes which can be extended to the directions intersecting with the axis A of the insertion member 120. The bearing can be formed, for example, by combining a roller bearing and a ball bearing.

Consequently, when removing the occluding object of the tubular-organ inside the living body, the blade edges formed on the rotation bodies can excavate the occluding object without facing the lumen wall. Thus, it can be possible to reduce damages of the lumen wall during the excavation.

In addition, when arranging the rotation bodies adjacent to each other, the rotation bodies can rotate in the same direction, so that the blade edges of the neighboring rotation bodies move to directions facing mutually and it can be possible to add a larger shearing force onto the occluding object between the neighboring rotation bodies, and it can be possible to grind the excavated object into smaller narrow slips and to make a situation in which the slips can be discharged easily to the outside of the body. Further, points at which the extended lines of the rotation axes of the rotation bodies intersect with the axis of the insertion member can be different respectively, so that the positions at which the blade edges of the rotation bodies excavate the occluding object can become different and it can become possible to realize an excavation of a broad area.

In other words, according to an exemplary embodiment of the present disclosure, it can be possible to excavate an occluding object of a tubular-organ inside a living body safely and also more efficiently, and to discharge the removed excavated object easily to the outside of the body.

For example, the excavated pieces of the occluding object can be ground by the upper-portion blade edges 154A to 154C and the lower-portion blade edges 156A to 156C and become narrower slips, and they can be introduced to a center opening portion 144 of the body 142 surrounding the first through third cones 152A-152C. Consequently, it can be possible to repress plugging of the center opening portion 144.

The first through third cones 152A-152C can be formed approximately in conically-shapes having tapers toward the rotation axes 158A to 158C and it can be possible for the upper-portion blade edges 154A to 154C and the lower-portion blade edges 156A to 156C to be bitingly-engaged with the occluding object excellently. In addition, the upper-portion blade edges 154A to 154C and the lower-portion blade edges 156A to 156C can be formed in gear shapes and can be arranged by being formed in trains at the outer circumferences of the top portions and the proximal portions of the first through third cones 152A-152C, in which there can be improved biting-engagement property with respect to the occluding object. It can be noted that it can be possible for the upper-portion blade edges 154A to 154C and the lower-portion blade edges 156A to 156C to be formed, for example, by mechanically processing the outer circumferences of the first through third cones 152A-152C or by being embedded thereinto.

As provided herein, certain details are described with respect to the exemplary first through third cones 152A-152C, according to an exemplary embodiment of the present disclosure.

For example, the blade trains of the upper-portion blade edges 154A to 154C and the lower-portion blade edges 156A to 156C in the first through third cones 152A-152C can be arranged adjacently mutually with the neighboring blade trains of the first through third cones 152A-152C. Therefore, it can become possible to hit the upper-portion blade edges 154A to 154C and the lower-portion blade edges 156A to 156C thoroughly from stem to stern without space with respect to the occluding object of the tubular-organ inside the living body.

In addition, the shapes of the first through third cones 152A-152C may not be identical cone shapes and each blade train can have a different cone angle so as to exert actions of blow and also compression and concurrently, actions of dragging and also scooping. In other words, e.g., the shapes of the upper-portion blade edges 154A-154C and the lower-portion blade edges 156A to 156C can be constituted so as to pull-in the excavated pieces of the occluding object of the tubular-organ inside the living body to the center opening portion along with the rotation of the first through third cones 152A-152C, and it can be possible to pull-in (collection) the excavated pieces efficiently.

In this exemplary embodiment, the first through third cones 152A-152C of the occluding object removal mechanism can be arranged at the body 142 freely rotatably, and also the drive device can be provided for driving the insertion member 120. The rotation of the first through third cones 152A-152C can be set such that the first through third cones 152A-152C can be rolled on the surface of the occluding object by rotating the insertion member 120 while compressing the first through third cones 152A-152C onto the occluding object of the tubular-organ inside the living body and by rotating the body 142 which can be arranged at the distal portion of the insertion member 120, and the occluding object can be to be cut by the lower-portion blade edges 156A to 156C and the upper-portion blade edges 154A-154C.

According to certain exemplary embodiments of the present disclosure, it can become unnecessary to provide the transmission device for rotationally driving the first through third cones 152A-152C and the drive shaft (e.g., proximal shaft and distal shaft) which can be interlinked to the transmission device, so that it can be possible to simplify the apparatus. In addition, there may not exist an interfering object (e.g., transmission device and drive shaft) in the vicinity of the center opening portion 144 of the body 142, so that it can be possible to collect the excavated pieces of the occluding object of the lumen inside the living body excellently. The lower-portion blade edges 156A to 156C of the first through third cones 152A-152C can be set to have shapes which cause the rotation easily when rotating the body 142 in a state of compressing the first through third cones 152A-152C onto the occluding object of the tubular-organ inside the living body.

As described herein, in this exemplary embodiment, the first through third cones can be arranged at the body so as to surround the circumference of the axis of the insertion member, and can include the rotation axes extending in the directions intersecting with the axis of the insertion member, so that the rotation directions of the blade edges arranged at the first through third cones can be identical. As an alternative or in addition, the top surfaces of the first through third cones can be adjacent mutually. Consequently, when removing the occluding object of the tubular-organ inside the living body, a state in which the blade edges arranged at the first through third cones can excavate the occluding object while bitingly-engaging with the occluding object, so that it can be possible to achieve stable removal of the occluding object. In other words, it can be possible to provide a catheter provided with a removal mechanism which can stably remove the occluding object of the lumen inside the living body.

Figure 9:
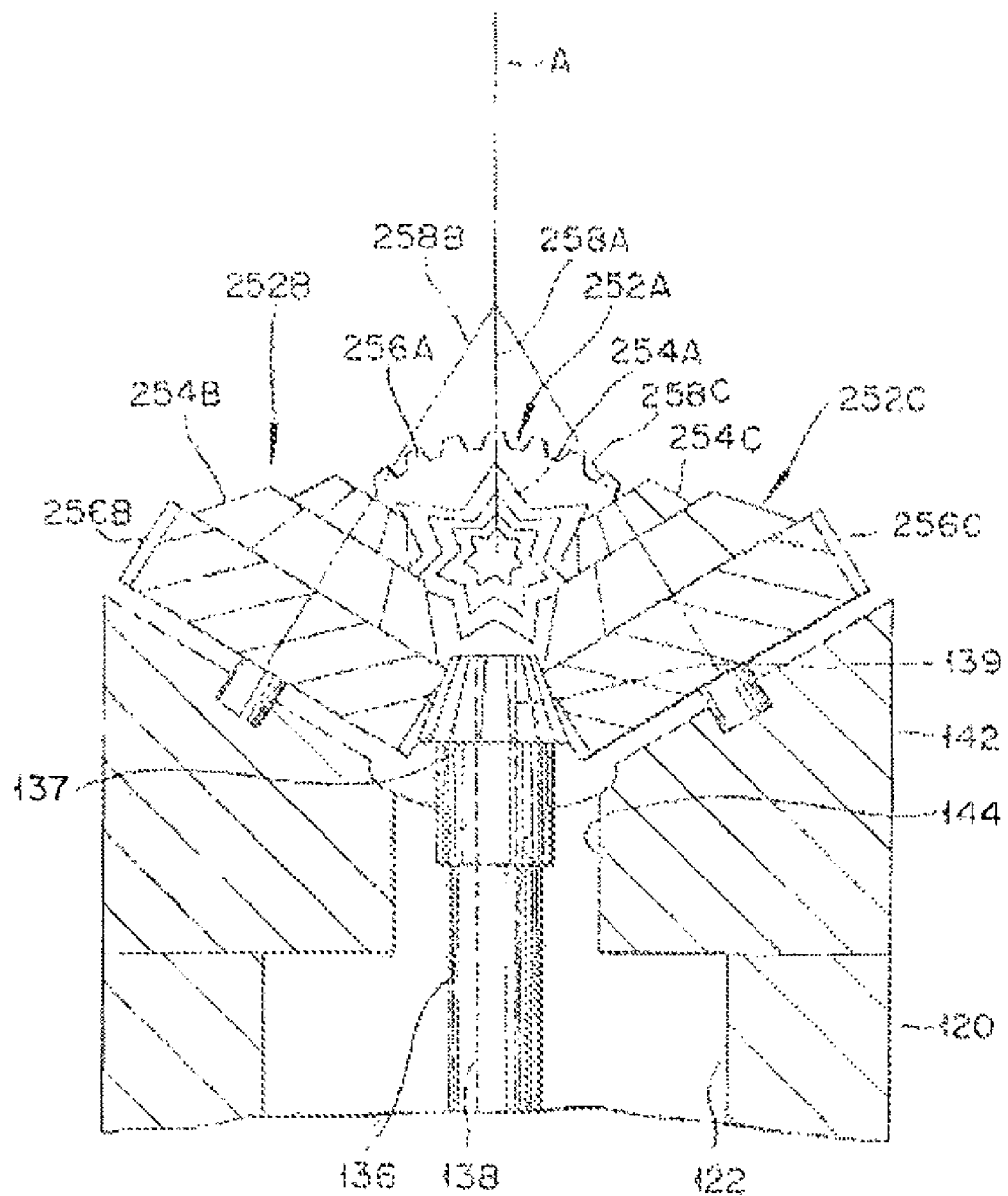
FIG. 9 is a cross-sectional view of an exemplary transmission device of the occluding object removal mechanism according to an exemplary embodiment of the present disclosure.
Figure 10:
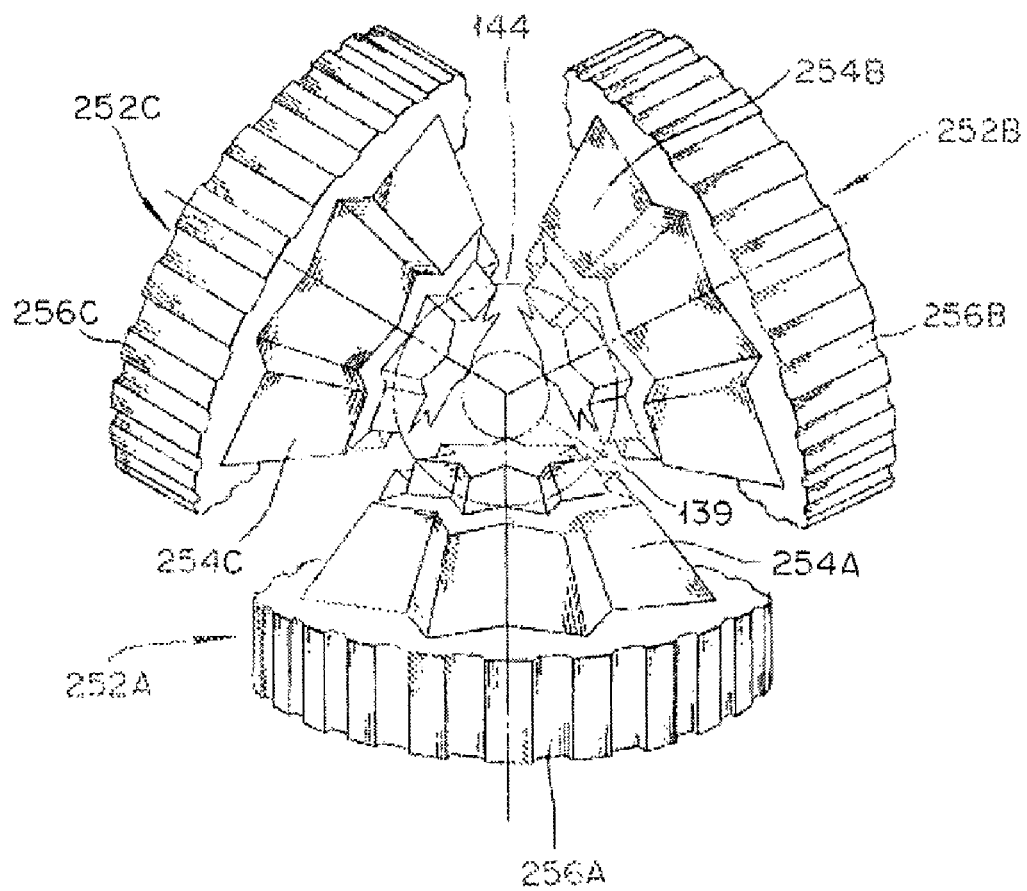
FIG. 10 is a perspective view of the exemplary occluding object removal mechanism shown in FIG. 9.

FIG. 9 shows a cross-sectional view showing an exemplary transmission device of an exemplary occluding object removal mechanism, and FIG. 10 illustrates a perspective view of the exemplary occluding object removal mechanism shown in FIG. 9.

In this exemplary embodiment illustrated in FIG. 9, a drive shaft 130 can be provided which can be arranged freely rotatably inside the lumen 122 of the insertion member 120 and the occluding object removal mechanism can include the transmission device for converting the rotation of the drive shaft 130 to the rotation of first through third cones 252A-252C, and a bevel gear 137 can be fixed at the distal portion of the drive shaft 130 (e.g., the distal shaft 136). The bevel gear 137 can be constituted so as to be bitingly-engaged with gears 256A to 256C respectively, which can have blade edges and which can be provided at the lower portions of the first through third cones 252A-252C, and it can be possible to make the transmission device as a simple structure. The bevel gear 137 can include a through-hole 139 which can be communicated with the lumen 138 of the distal shaft 136 and can be set so as not to interfere with the collection of the excavated pieces, which can utilize the lumen 138 of distal shaft 136.

The first through third cones 252A-252C can be arranged, for example, at the body 142 freely rotatably through bearings, and can be position-set so as to surround the circumference of an axis A of the insertion member 120, and the first through third cones 252A-252C can include upper-portion blade edges 254A-254C which can be arranged at the outer circumferences of the top portions thereof, lower-portion blade edges 256A-256C which can be arranged at the outer circumferences of the proximal portions thereof and rotation axes 258A-258C which can be extended to the directions intersecting with the axis A of the insertion member 120. The bearing can be formed, for example, by combining a roller bearing and a ball bearing.

Consequently, this exemplary embodiment can exert a similar effect as that of the other exemplary embodiments and concurrently, it can be possible to directly drive the first through third cones 252A-252C by the drive device 180, so that even for a soft occluding object in which it can be difficult for the cones to rotate only by rotating the insertion member 120 in a state of compressing the cones thereon, it can be possible to achieve the excavation safely and also efficiently, and it can be possible to discharge the removed excavated object easily to the outside of the body.

The exemplary embodiments of the present disclosure are not limited by the above-mentioned exemplary embodiments and it is possible to be modified variously within the scope of the claims. For example, the tubular-organ inside the living body is not limited by the blood vessel and it can be also possible to be applied to a biliary tract for transporting bile to an intestinal tract. In this case, the occluding object of the biliary tract can be a gallstone (e.g., calculus) which can include, for example, a cholesterol calculus (e.g., pure cholesterol stone, combination stone, cholesterol pigment lime stone or mixed stone). In addition, the occluding object removal mechanism is not limited by the configuration including three cones and it can be also possible to include two cones, or four or more cones appropriately. All publications referenced herein are incorporated herein by reference in their entireties.

EXEMPLARY REFERENCE NUMERALS

10: exemplary living body,
20: exemplary tubular-organ,
30: exemplary occluding object,
100: exemplary catheter,
110: exemplary sheath portion,
112: exemplary lumen,
114: exemplary Y-shaped adaptor,
116: exemplary branch port,
118: exemplary sealing device,
120: exemplary insertion member,
122: exemplary lumen,
124: exemplary Y-shaped adaptor,
126: exemplary branch port,
128: exemplary sealing device,
130: exemplary drive shaft,
132: exemplary proximal shaft,
134: exemplary lumen,
135: exemplary opening portion,
136: exemplary distal shaft,
137: exemplary bevel gear,
138: exemplary lumen,
139: exemplary through-hole,
140: exemplary occluding object removal mechanism,
142: exemplary body,
144: exemplary center opening portion,
150: exemplary roller hit,
152A-152C: exemplary the first to third cones,
154A to 154C: exemplary upper-portion blade edge,
156A to 156C: exemplary lower-portion blade edge,
158A to 158C: exemplary rotation axis,
160: exemplary excavated-piece suction system,
162: exemplary suction pump,
170: exemplary liquid discharge system,
172: exemplary discharge pump,
174: exemplary flow path,
180: exemplary drive device,
252A-252C: exemplary first to third cones,
254A to 254C: exemplary upper-portion blade edge,
256A to 256C: exemplary lower-portion blade edge,
258A to 258C: exemplary rotation axis.

What is claimed is:

1. A catheter for excavating at least one occluding object from a tubular organ, comprising:
a sheath portion which (i) has a first elongated lumen provided therein, and (ii) is insertable into the tubular organ inside a body;
an insertion member which (i) has a second elongated lumen provided therein, and (ii) is arranged free, slidably, and rotatably with respect to the first elongated lumen of the sheath portion; and
a removal mechanism configured to remove the at least one occluding object of the tubular organ, wherein
the removal mechanism includes a support portion arranged at a distal portion of the insertion member and a plurality of rotating arrangements (i) provided at the support portion and (ii) having at least one blade edge configured to excavate the at least one occluding object, and
at least one of the plurality of rotating arrangements has an axis of rotation that intersects an axis of extension of the insertion member.

2. The catheter according to claim 1, wherein each of the rotating arrangements has an approximately conical shape with a taper toward a distal end of the axis of rotation.

3. The catheter according to claim 2, wherein the at least one blade edge of at least one of the rotating arrangement (i) has a shape of a gear, and (ii) is shaped by forming a blade train, and wherein the blade train of at least one of the rotating arrangement is arranged so as to rotate mutually independently with respect to a blade train of a neighboring one of the rotating arrangements.

4. The catheter according to claim 1, further comprising an excavated-piece suction arrangement provided in communication with the second elongated lumen, wherein
the removal mechanism includes a center opening portion in communication with the second elongated lumen, and
each of the rotating arrangements is positioned at a circumference of the center opening portion.

5. The catheter according to claim 4, wherein a shape of a blade edge of each of the rotating arrangements is configured or structured so as to pull-in excavated pieces of the occluding object toward the center opening portion along with the rotation of a respective of the rotating arrangements.

6. The catheter according to claim 4, further comprising a liquid discharge arrangement configured to discharge liquid at a distal portion of the sheath portion, wherein the liquid discharge arrangement includes a flow path that includes a space formed between the first elongated lumen of the sheath portion and an outer circumference of the insertion member.

7. The catheter according to claim 1, wherein, when the removal mechanism is compressed onto the at least one occluding object by projecting the insertion member from the sheath portion, the rotating arrangements of the removal mechanism rotate and excavate the at least one occluding object, and the excavated object is fed into the second elongated lumen.

8. A catheter for removing at least one occluding object from a tubular organ, comprising:
an insertion member which (i) has at least one elongated lumen disposed therein, and (ii) is insertable into the tubular organ inside a body;
a hollow drive shaft arranged freely rotatably inside the at least one elongated lumen of the insertion member; and
a removal mechanism configured to remove the at least one occluding object of the tubular organ inside the body, wherein
the removal mechanism includes (i) a support portion arranged at a distal portion of the insertion member, (ii) a plurality of rotating arrangements arranged at the support portion and provided with blade edges for excavating the at least one occluding object, and (iii) a transmission arrangement configured to convert a rotation of the drive shaft to each of the rotating arrangements, and
at least one of the plurality of rotating arrangements includes an axis of rotation that intersects an axis of extension of the insertion member.

9. The catheter according to claim 8, wherein the transmission arrangement includes a bevel gear arranged at a distal portion of the drive shaft.

10. The catheter according to claim 8, further comprising:
a further elongated lumen disposed within the drive shaft and including an opening portion by which excavated pieces of the at least one occluding object are pulled-in; and an excavated-piece suction arrangement in communication with the elongated lumen of the insertion member and the further elongated lumen of the drive shaft, wherein the support portion of the removal mechanism including a center opening portion in communication with the elongated lumen of the insertion member.

11. The catheter according to claim 8, wherein, when the removal mechanism is compressed onto the at least one occluding object and the drive shaft is rotated, each of the rotating arrangements of the removal mechanism rotates and excavates the at least one occluding object, and the at least one excavated object is fed into the elongated lumen of the insertion member and the drive shaft.

\* \* \* \* \*